(12) United States Patent
Natti

(10) Patent No.: US 6,355,868 B1
(45) Date of Patent: Mar. 12, 2002

(54) INBRED SWEET CORN LINE I874WS

(75) Inventor: Thomas A. Natti, Meridian, ID (US)

(73) Assignee: Harris Moran Seed Company, Modesto, CA (US)

(*) Notice: Subject to any disclaimer, the term of this patent is extended or adjusted under 35 U.S.C. 154(b) by 0 days.

(21) Appl. No.: 09/505,863

(22) Filed: Feb. 17, 2000

(51) Int. Cl.$^7$ .............................. A01H 5/00; A01H 5/10; A01H 1/02; A01H 1/04
(52) U.S. Cl. .................... 800/320.1; 800/263; 800/265; 800/266; 800/267; 800/268; 800/274; 800/275; 800/278; 800/279; 800/284; 800/300.1; 800/302; 800/303; 435/69.1; 435/412; 435/418; 435/419; 435/424; 435/430; 435/430.1; 435/468
(58) Field of Search ................................. 800/263, 265, 800/266, 267, 268, 274, 275, 278, 279, 284, 300.1, 302, 303, 320.1; 435/69.1, 412, 418, 419, 421, 424, 430, 430.1, 468

(56) References Cited

U.S. PATENT DOCUMENTS 6,184,438 B1 * 2/2001 Hannah ...................... 800/284

* cited by examiner

*Primary Examiner*—David T. Fox
(74) *Attorney, Agent, or Firm*—Rothwell, Figgs, Ernst & Manbeck

(57) ABSTRACT

An inbred sweet corn line, designated I874WS, is disclosed. The invention relates to the seeds of inbred corn line I874WS, to the plants of inbred corn line I874WS and to methods for producing a corn plant produced by crossing the inbred line I874WS with itself or another corn line. The invention further relates to hybrid corn seeds and plants produced by crossing the inbred line I874WS with another corn line.

28 Claims, No Drawings

INBRED SWEET CORN LINE I874WS

BACKGROUND OF THE INVENTION

The present invention relates to a new and distinctive sweet corn inbred line, designated I874WS. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, improved flavor, tolerance to drought and heat, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s). The best lines are candidates for new commercial cultivars; those elite in traits are used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior sweet corn inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new sweet corn inbred line.

The development of commercial sweet corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complimentary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parents is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Sweet corn is an important and valuable vegetable crop. Thus, a continuing goal of plant breeders is to develop stable, high yielding sweet corn hybrids that are agronomically sound. The reasons for this goal are obviously to maximize the amount of ears and kernels produced on the land used and to supply food for humans. To accomplish this goal, the sweet corn breeder must select and develop sweet corn plants that have the traits that result in superior parental lines for producing hybrids.

SUMMARY OF THE INVENTION

According to the invention, there is provided a novel inbred corn line, designated I874WS. This invention thus relates to the seeds of inbred corn line I874WS, to the plants of inbred corn line I874WS and to methods for producing a corn plant produced by crossing the inbred line I874WS with itself or another corn line. This invention further relates to hybrid corn seeds and plants produced by crossing the inbred line I874WS with another corn line.

The inbred corn plant of the invention may further comprise, or have, a cytoplasmic factor that is capable of conferring male sterility. Parts of the corn plant of the present invention are also provided, such as e.g., pollen obtained from an inbred plant and an ovule of the inbred plant.

In one aspect, the present invention provides for single gene converted plants of I874WS. The single transferred gene may preferably be a dominant or recessive allele. Preferably, the single transferred gene will confer such traits as male sterility, herbicide resistance, insect resistance, resistance for bacterial, fungal, or viral disease, male fertility, enhanced nutritional quality, and industrial usage. The single gene may be a naturally occurring maize gene or a transgene introduced through genetic engineering techniques.

In another aspect, the present invention provides regenerable cells for use in tissue culture or inbred corn plant I874WS. The tissue culture will preferably be capable of regenerating plants having the physiological and morphological characteristics of the foregoing inbred corn plant, and of regenerating plants having substantially the same genotype as the foregoing inbred corn plant. Preferably, the regenerable cells in such tissue cultures will be embryos, protoplasts, meristematic cells, callus, pollen, leaves, anthers, roots, root tips, silk, kernels, ears, cobs, husks or stalks. Still further, the present invention provides corn plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Allele. The allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Endosperm Type. Endosperm type refers to endosperm genes and types such as starch, sugary alleles (su1, su2, etc.), sugary enhancer or extender, waxy, amylose extender, dull, brittle alleles (bt1, bt2, etc.), other sh2 alleles, and any combination of these.

Essentially all the physiological and morphological characteristics. A plant having essentially all the physiological and morphological characteristics means a plant having the physiological and morphological characteristics, except for the characteristics derived from the converted gene.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

DETAILED DESCRIPTION OF THE INVENTION

Inbred sweet corn line I874WS is a white sweet corn with a sh2 endosperm and superior characteristics, and provides an excellent parental line in crosses for producing first generation ($F_1$) hybrid sweet corn.

I874WS is a sweet corn inbred line developed from the cross of 1815S x Purdue 118W. This cross was then backcrossed twice to inbred 1815S and selfed using the pedigree method of plant breeding. Northern leaf blight resistance, common rust resistance, Florida adaptability, yield, eating quality, good husk characteristics, plant habitat, disease tolerance, maturity, emergence and vigor, ear shape, and produceability, were the criteria used to determine the rows from which ears were selected.

Inbred sweet corn line I874WS has the following morphologic and other characteristics (based primarily on data collected at Nampa, Idaho).

| VARIETY DESCRIPTION INFORMATION | |
|---|---|
| 1. TYPE: Inbred | |
| 2. REGION WHERE DEVELOPED: Nampa, Idaho | |
| 3. VIGOR: (1 = very weak–5 = very strong): | 2.8 |
| 4. MATURITY: | |
| | Days |
| From planting to 50% of plants in tassel: | 72 |
| From planting to 50% of plants in silk: | 75 |
| 5. PLANT: | |
| Plant Height (to tassel tip): | 165.1 cm |
| Ear Height (to base of top ear): | 64.0 cm |
| Average number of Tillers: | 1.1 |
| Average Number of Ears per Stalk: | 1.1 |
| Anthocyanin Markings: | None |
| 6. LEAF: | |
| Width of Ear Node Leaf: | 9.75 cm |
| Length of Ear Node Leaf: | 80.0 cm |
| Leaf Angle from 2nd leaf above ear: | 80° |
| Leaf Sheath Pubescence (1 = none–5 = peach fuzz): | 2 |
| Marginal waves (1 = none–5 = many): | 4 |
| Longitudinal Creases (1 = none–5 = many): | 1 |
| 7. TASSEL: | |
| Number of Tassel Branches: | 18.8 |
| Branch Angle from Central Spike: | 100° |
| Tassel Length (from top leaf collar to tassel top): | 35.7 cm |
| Anther Color: | Yellow |
| Glume Color: | Green |
| 8. EAR: | |
| Silk color (3 days after emergence): | Yellow |
| Husk Extension: | 6.3 cm |
| Number of flag leaves: | 5.2 |
| Average length of flag: | 5.85 cm |
| Average width of flag: | 1.1 cm |
| Ear Length: | 15.6 cm |
| Ear Diameter at mid-point: | 4 cm |
| Number of Kernel Rows: | 14.6 |
| Row Straightness (1 = very scrambled–5 = perfectly straight): | 2.8 |
| Shank Length: | 7.7 cm |
| Shape: | Tapered tip and butt |
| 9. KERNEL: | |
| Color: | White |
| Endosperm Type: | sh2 |
| 10. COB: | |
| Cob Color: | White |
| 11. DISEASE RESISTANCE | |
| Rating (1 = susceptible–5 = resistant) | |
| 4.5 Common Rust | |
| 2.6 Maize Dwarf Mosaic | |
| 4.8 Northern Leaf Blight | |
| 5.0 Stewart's Wilt Resistance | |

This invention is also directed to methods for producing a corn plant by crossing a first parent corn plant with a second parent corn plant, wherein the first or second corn plant is the inbred corn plant from the line I874WS. Further, both first and second parent corn plants may be from the inbred line I874WS. Therefore, any methods using the inbred corn line I874WS are part of this invention: selfing, backcrosses, hybrid breeding, and crosses to populations. Any plants produced using inbred corn line I874WS as a parent are within the scope of this invention. Advantageously, the inbred corn line is used in crosses with other corn varieties to produce first generation ($F_1$) corn hybrid seed and plants with superior characteristics.

As used herein, the term "plant" includes plant cells, plant protoplasts, plant cell of tissue culture from which corn plants can be regenerated, plant calli, plant clumps, and plant cells that are intact in plants or parts of plants, such as pollen, flowers, kernels, ears, cobs, leaves, husks, stalks, and the like.

The present invention contemplates a corn plant regenerated from a tissue culture of an inbred (e.g., I874WS) or hybrid plant of the present invention. As is well known in the art, tissue culture of corn can be used for the in vitro regeneration of a corn plant. By way of example, a process of tissue culturing and regeneration of corn is described in European Patent Application, publication 160,390, the disclosure of which is incorporated by reference. Corn tissue culture procedures are also described in Green & Rhodes (I 982) and Duncan, et al., (1985). The study by Duncan et al., (1985) indicates that 97 percent of cultured plants produced calli capable of regenerating plants. Subsequent studies have shown that both inbreds and hybrids produced 91 percent regenerable calli that produced plants.

Other studies indicate that non-traditional tissues are capable of producing somatic embryogenesis and plant regeneration. See, e.g., Songstad et al., (1988); Rao et al., (1986); and Conger et al., (1987), the disclosures of which are incorporated herein by reference. Regenerable cultures may be initiated from immature embryos as described in PCT publication WO 95/06128, the disclosure of which is incorporated herein by reference.

Thus, another aspect of this invention is to provide for cells which upon growth and differentiation produce the inbred line I874WS.

I874WS is most similar to FAHT 32B, however, there are numerous differences including the kernel color.

I874WS has white kernels and produces a taller plant. This increased plant size is useful for hybrids grown during the winter season in Florida, as overall plant and ear size are usually smaller during this growing season. Seed quality and seedling vigor are improved in I874WS. Common rust resistance and stronger Northern Leaf Blight resistance were selected as well as tolerance to MDMV and Stewart's Wilt. This combination of disease resistance/tolerance is not common among sweet corn inbreds or hybrids, especially with white kernels. I874WS combines well and is best suited for hybrids that are used in the shipping trade. A more slender ear, longer husk cover, attractive husk color and flag leaves contribute to hybrids with these features that are important for shipping hybrids. For seed production, I874WS is well suited for a female or male.

The inbred has shown uniformity and stability. It has been self-pollinated and ear-rowed a sufficient number of generations, with careful attention to uniformity of plant type to ensure homozygosity and phenotypic stability. The line has been increased both by hand and sibbed in isolated fields with continued observations for uniformity. No variant traits have been observed or are expected in I874WS.

Table

In the table that follows, the traits and characteristics of inbred sweet corn line I874WS are given in hybrid combination along with data on commercial check hybrids. The first two hybrids listed in each table are the hybrids containing I874WS as one parent. Candy Store and Sweet Symphony are commercial check hybrids. Information for the hybrids includes the following traits:

In the Tables, Columns 1 and 2 list the Hybrid and location where grown.

Column 3 shows the days to silk (SILK) which are based on the number of days from planting until 50% of the plants show silk.

Column 4 shows the ear length (LGTH) in centimeters for each of the hybrids and commercial checks.

Column 5 gives the ears/plant (E/P) score and is recorded by using a scoring system of 1–5, defined as follows:

1=No marketable ears/plant
3=1 marketable ear/plant
5=2 marketable ears/plant

Column 6 gives the tip fill (TIP) score and is recorded by using a scoring system of 1–5, defined as follows:

1=>5 cm blank tip
2=5 cm blank tip
3=2.5 cm blank tip
4=1.5 cm blank tip
5=no blank tip, perfect tip fill

| Yield Data for 1999 | | | | | |
|---|---|---|---|---|---|
| Hybrid | Location | SILK | LGTH | E/P | TIP |
| 1853S × 1874WS | Nampa, ID | 72 | 21.0 | 3.0 | 5.0 |
| 1853S × 1874WS | Hall, NY | 60 | 20.8 | 3.0 | 4.5 |
| 1853S × 1874WS | Sun Prairie, WI | 57 | 19.0 | 3.0 | 4.8 |
| 1853S × 1874WS | Belle Glade, FL | 58 | 16.0 | 2.8 | 4.5 |
| 1853S × 1874WS | Davis, CA | 59 | 17.4 | 3.0 | 5.0 |
| Average | | 61.2 | 18.8 | 3.0 | 4.8 |
| 1880S × 1874WS | Nampa, ID | 68 | 20.0 | 3.0 | 4.5 |
| 1880S × 1874WS | Hall, NY | 57 | 19.8 | 3.0 | 3.8 |
| 1880S × 1874WS | Sun Prairie, WI | 62 | 20.0 | 3.0 | 4.8 |
| 1880S × 1874WS | Belle Glade, FL | 55 | 18.6 | 3.3 | 4.3 |
| 1880S × 1874WS | Davis, CA | 55 | 18.6 | 3.3 | 4.3 |
| Average | | 60 | 19.5 | 3.0 | 4.4 |
| Candy Store | Nampa, ID | 68 | 21.0 | 3.0 | 4.8 |
| Candy Store | Hall, NY | 58 | 19.0 | 3.0 | 4.8 |
| Candy Store | Sun Prairie, WI | 66 | 20.5 | 3.0 | 4.9 |
| Candy Store | Belle Glade, FL | 57 | 18.8 | 3.0 | 4.5 |
| Candy Store | Davis, CA | 54 | 19.0 | 3.0 | 3.5 |
| Average | | 60.6 | 19.7 | 3.0 | 4.5 |
| Sweet Symphony | Nampa, ID | 66 | 18.0 | 3.0 | 4.8 |
| Sweet Symphony | Hall, NY | 50 | 19.0 | 3.3 | 4.0 |
| Sweet Symphony | Sun Prairie, WI | 67 | 18.5 | 3.0 | 4.5 |
| Sweet Symphony | Davis, CA | 54 | 18.6 | 3.3 | 5.0 |
| Sweet Symphony | Preston, MD | 67 | 16.8 | 4.0 | 4.3 |
| Average | | 60.8 | 18.2 | 3.3 | 4.5 |

When the term inbred corn plant is used in the context of the present invention, this also includes any single gene conversions of that inbred. The term single gene converted plant as used herein refers to those corn plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental corn plants for that inbred. The parental corn plant which contributes the gene for the desired characteristic is termed the nonrecurrent or donor parent. This terminology refers to the fact that the nonrecurrent parent is used one time in the backcross protocol and therefore does not recur. The parental corn plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

A further aspect of the invention relates to tissue culture of corn plants designated I874WS. As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, kernels, ears, cobs, leaves, husks, stalks, roots, root tips, anthers, silk and the like. In a preferred embodiment, tissue culture is embryos, protoplast, meristematic cells, pollen, leaves or anthers. Means for preparing and maintaining plant tissue culture are well known in the art. By way of example, a tissue culture comprising organs such as tassels or anthers, has been used to produce regenerated plants. (See U.S. Pat. Nos. 5,445,961; 5,322,789; 5,948,957 and 5,969,212, the disclosures of which are incorporated herein by reference).

Deposit Information

A deposit of the Harris Moran Seed Company inbred sweet corn line I874WS disclosed above and recited in the appended claims has been made with the American Type Culture Collection (ATCC), 10801 University Boulevard, Manassas, Va. 20110. The date of deposit was Oct. 4, 2001. The deposit of 2,500 seeds were taken from the same deposit maintained by Harris Moran Seed Company since prior to the filing date of this application. All restrictions upon the deposit have been removed, and the deposit is intended to meet all of the requirements of 37 C.F.R. §1.801–1.809. The ATCC accession number is PTA-3755. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. An inbred corn seed designated I874WS, a sample of said seed having been deposited under ATCC Accession No. PTA-3755.

2. A corn plant, or parts thereof, produced by growing the seed of claim 1.

3. Pollen of the plant of claim 2.

4. An ovule of the plant of claim 2.

5. A corn plant, or parts thereof, having all of the physiological and morphological characteristics of the corn plant of claim 2.

6. A tissue culture of regenerable cells of a corn plant of inbred line I874WS, wherein the tissue regenerates plants having all the morphological and physiological characteristics of the inbred line I874WS.

7. A tissue culture according to claim 6, the cells being derived from a member of the group consisting of leaves, pollen, embryos, roots, root tips, anthers, silks, flowers, kernels, ears, cobs, husks, and stalks.

8. A corn plant regenerated from the tissue culture of claim 6, having all the morphological and physiological characteristics of inbred line I874WS.

9. A method for producing a hybrid corn seed comprising crossing a first inbred parent corn plant with a second inbred parent corn plant and harvesting the resultant hybrid corn seed, wherein said first or second parent corn plant is the corn plant of claim 2.

10. A hybrid corn seed produced by the method of claim 9.

11. A hybrid corn plant, or parts thereof, produced by growing said hybrid corn seed of claim 10.

12. Corn seed produced by growing said hybrid corn plant of claim 11.

13. A corn plant, or parts thereof, produced from seed of claim 12.

14. A method for producing a hybrid corn seed comprising crossing an inbred plant according to claim 2 with another, different corn plant.

15. A hybrid corn seed produced by the method of claim 14.

16. A hybrid corn plant, or its parts, produced by growing said hybrid corn seed of claim 15.

17. Corn seed produced from said hybrid corn plant of claim 16.

18. A corn plant, or its parts, produced from the corn seed of claim 17.

19. A method for producing a I874WS-derived corn plant, comprising:
   a) crossing inbred corn line I874WS, a sample of seed of said line having been deposited under ATGC accession number PTA-3755, with a second maize plant to yield progeny corn seed;
   b) growing said progeny corn seed, under plant growth conditions, to yield said I874WS-derived corn plant.

20. The method of claim 19, further comprising:
   c) crossing said I874WS-derived corn plant with itself or another corn plant to yield additional I874WS-derived progeny corn seed;
   d) growing said progeny corn seed of step (c) under plant growth conditions, to yield additional I874WS-derived corn plants;
   e) repeating the crossing and growing steps of (c) and (d) from 0 to 7 times to generate further I874WS-derived corn plants.

21. The method of claim 20, still further comprising utilizing plant tissue culture methods to derive progeny of said I874WS-derived corn plant.

22. The corn plant, or parts thereof, of claim 2, wherein the plant or parts thereof have been transformed so that its genetic material contains one or more transgenes operably linked to one or more regulatory elements.

23. A method for producing a corn plant that contains in its genetic material one or more transgenes, comprising crossing the corn plant of claim 22 with either a second plant of another corn line, or a non-transformed corn plant of the line I874WS, so that the genetic material of the progeny that result from the cross contains the transgene(s) operably linked to a regulatory element.

24. Corn plants, or parts thereof, produced by the method of claim 23.

25. The corn plant of claim 5, further comprising a single gene conversion.

26. The corn plant of claim 25, further comprising a cytoplasmic factor conferring male sterility.

27. The single gene conversion corn plant of claim 25, where the gene is selected from the group consisting of: a transgene, a dominant allele, and a recessive allele.

28. The single gene conversion corn plant of claim 25, where the gene confers a characteristic selected from the group consisting of: herbicide resistance; insect resistance; resistance to bacterial, fungal, or viral disease; male sterility; endosperm type; and improved nutritional quality.

* * * * *